(12) United States Patent
Grimmond et al.

(10) Patent No.: US 7,205,385 B2
(45) Date of Patent: Apr. 17, 2007

(54) POLYMERIZATION METHOD FOR THE SYNTHESIS OF POLYPEPTIDE IMAGING AGENTS

(75) Inventors: Brian James Grimmond, Clifton Park, NY (US); Bahram Moasser, Schenectady, NY (US); Mohan Mark Amaratunga, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/987,662

(22) Filed: Nov. 12, 2004

(65) Prior Publication Data

US 2006/0104908 A1 May 18, 2006

(51) Int. Cl.
- C07K 1/04 (2006.01)
- C07K 2/00 (2006.01)
- A61K 38/00 (2006.01)
- A61K 38/02 (2006.01)

(52) U.S. Cl. .......................... 530/333; 514/2; 530/300
(58) Field of Classification Search ...................... None
See application file for complete search history.

(56) References Cited

U.S. PATENT DOCUMENTS

| | | | |
|---|---|---|---|
| 4,604,463 A * | 8/1986 | Miyasaka et al. | 544/125 |
| 5,210,075 A * | 5/1993 | Scholz et al. | 514/14 |
| 5,230,883 A | 7/1993 | Kornguth et al. | |
| 5,414,114 A * | 5/1995 | Palacios | 562/556 |
| 5,607,659 A * | 3/1997 | Gustavson et al. | 424/1.73 |
| 5,762,909 A | 6/1998 | Uzgiris | |
| 6,235,264 B1 | 5/2001 | Uzgiris | |
| 6,512,092 B2 * | 1/2003 | Falb et al. | 530/333 |
| 6,680,365 B1 | 1/2004 | Deming | |
| 6,685,915 B2 | 2/2004 | Uzgiris et al. | |
| 2001/0028877 A1 | 10/2001 | Uzgiris | |
| 2004/0022857 A1 | 2/2004 | Uzgiris et al. | |
| 2004/0097403 A1 * | 5/2004 | Ranganathan et al. | 514/2 |
| 2004/0265235 A1 * | 12/2004 | Uzgiris et al. | 424/9.322 |

FOREIGN PATENT DOCUMENTS

| | | |
|---|---|---|
| GB | 1210719 A * | 10/1970 |
| JP | 60015425 | 1/1985 |

OTHER PUBLICATIONS

E.E. Uzgiris, et al. Biomacromolecules (2004) 5, pp. 54-61.*
R. M. Cicchillo and P. Norris. Carb. Res. (2000) 328, pp. 431-434.*
L. Lemoucheux, et al. J. Org. Chem. (2003) 68, pp. 7289-7297.*
F. Bigi, et al. Green Chemistry (2000) 2, pp. 140-148.*
L. Fabrizi, et al. Chem. Res. Toxicol. (2003) 16, pp. 266-275.*
C. Yu and J. Kohn. Biomaterials (1999) 20, pp. 253-264.*
Copending U.S. Appl. No. 10/609,269, filed Jun. 26, 2003, entitled "Magnetic Resonance Contrast-Enhancing Agents and Method for Detecting and Imaging Artherosclerotic Plaque."
Wilbur et al, "Biotin Reagents for Antibody Pretargeting. 3. Synthesis, Radioiodination, and Evaluation of Biotinylated Starburst Dendrimers", *Bioconjugate Chem.* 9, 813-825 (1998).
Tsai et al, "Metabolism and Renal Clearance of $^{111}$In-Labeled DOTA-Conjugated Antibody Fragments", *Bioconjugate Chem.* 12, 264-270 (2001).
Sieving et al., "Preparation and Characterization of Paramagnetic Polychelates and Their Protein Conjugates", *Bioconjugate Chem.* 1(1), 65-71 (1990).
Deming, "Facile synthesis of block copolypeptides of defined architecture", *Nature* 390, 386-389 (1997).
Deming, "Cobalt and Iron Initiators for the Controlled Polymerization of α-Amino Acid-N-Carboxyanhydrides", *Macromolec.* 32, 4500-4502 (1999).
Okada et al., "Synthesis of Glycopeptide-conjugates via Ring-opening Polymerization of Sugar-substituted α-Amino Acid N-Carboxyanhydrides (GlycoNCAs)", *Proc. Japan Acad.* 73 (Ser. B), 205-209 (1997).
Hirschmann et al., "The Controlled Synthesis of Peptides in Aqueous Medium. The Preparation and Use of Novel α-Amino Acid N-Carboxyanhydrides", *J. Amer. Chem. Soc.* 93:11, 2746-2754 (1971).
Fuller, et al., "Urethane-Protected α-Amino Acid N-Carboxyanhydrides and Peptide Synthesis", *Biopolymers (Peptide Science)* vol. 40, 183-205 (1996).
Dent III et al., "9-BBN: An Amino Acid Protecting Group for Functionalization of Amino Acid Side Chains in Organic Solvents", *Org. Lett.* 4 (8), 1249-1251 (2002).

* cited by examiner

*Primary Examiner*—Cecilia J. Tsang
*Assistant Examiner*—Andrew D. Kosar
(74) *Attorney, Agent, or Firm*—Maureen A. Bresnahan; Jean K. Testa

(57) ABSTRACT

A method for synthesizing extended poly(amino acids) conjugated to imaging agents, such as DTPA, is disclosed. The amino acid is initially conjugated to the imaging agent at the monomer stage, followed by formation of the corresponding N-carboxyanhydride. The method utilizes catalyzed ring opening polymerization of the N-carboxyanhydride of the amino acid-imaging agent monomer allowing the formation of a poly(amino acid) backbone having 100% imaging agent conjugation if desired. However, the present method also permits the degree of conjugation to be controlled by copolymerizing the N-carboxyanhydride of the amino acid-imaging agent monomer with one or more unconjugated monomers, i.e. N-carboxyanhydrides of the same or of other amino acids. Various imaging agents may be employed, and new hybrid random, block, and mixed copolymers may be prepared.

28 Claims, No Drawings

POLYMERIZATION METHOD FOR THE SYNTHESIS OF POLYPEPTIDE IMAGING AGENTS

CROSS-REFERENCE TO RELATED APPLICATIONS

This Application claims priority to U.S. Ser. No. 10/609,269, filed Jun. 26, 2003, entitled, "MAGNETIC RESONANCE CONTRAST-ENHANCED AGENTS AND METHOD FOR DETECTING AND IMAGING ARTHEROSOLEROTIC PLAQUE"; and U.S. Ser. No. 10/209,726, filed Jul. 31, 2002, published Feb. 5, 2004 under Publication No. US 2004/0022857 A1, entitled "SYNTHESIS OF HIGHLY CONJUGATED POLYMERS", now abandoned; the disclosures of which are incorporated by reference herein in their entireties.

BACKGROUND OF THE INVENTION

The present invention relates to magnetic resonance imaging, and more particularly to a method for preparing magnetic resonance imaging agents.

Magnetic resonance imaging (MRI) is an important technique for detecting abnormalities in a patient's body, thereby aiding in the diagnosis and treatment of certain diseases. MRI is advantageous because it is noninvasive, and there is no exposure to harmful radiation. Using MRI, normal and diseased tissues may be differentiated on the basis of differences in relaxation times, $T_1$ or $T_2$ wherein $T_1$ refers to the spin-lattice or longitudinal relaxation time, and $T_2$ refers to the spin-spin or transverse relaxation time. In some cases, however, the abnormal tissues have the same relaxation times as the normal tissues.

MRI contrast-enhancing agents enhance various portions of the MR image by changing, usually increasing, the relaxation rate of bulk water protons in close proximity to the agent. Thus, the imaging contrasts between normal and abnormal tissues are enhanced. Low molecular weight contrast-enhancing agents, such as gadolinium (III) diethylenetriaminepentaacetic acid (Gd.DTPA) (MW=538), have been widely used for this purpose because they can diffuse rapidly into plaques. However, due to their small molecular size, they also tend to clear away rapidly from the body. Thus, the imaging procedure must be completed within a very short time after such agents are administered into a patient. In addition, these low molecular-weight agents deliver only a limited number of contrast-enhancing ions to the region of interest.

The introduction of high molecular weight MRI contrast-enhancing agents using natural and synthetic macromolecules into the circulation remain longer, providing ample time to migrate across the tumor endothelium. These agents also easily diffuse through the endothelial layer of the tumor. Such agents comprise multiple chelating groups, such as DTPA, coupled to a singular polymer backbone, such as a poly(amino acid). These chelating moieties also form coordination complexes with paramagnetic cations, such as gadolinium (III), dysprosium (III), holmium (III), europium (III), iron (III), or manganese (II). For example, poly(1-lysine-Gd.DTPA), has been shown to be an excellent MRI contrast-enhancing agent.

These high molecular weight contrast-enhancing agents bearing a poly(amino acid) backbone conjugated to chelating moieties complexed with paramagnetic ions demonstrate selective association and imaging of diseased tissue making them useful for detecting tumors, for example. The tissue selectivity and imaging intensity of these agents is believed to rely on a high degree of conjugation of the poly(amino acid) repeat units with the gadolinium (Gd) (or other paramagnetic ion) chelator. However, highly conjugated polymers, such as conjugated poly(1-lysine-Gd.DTPA), are difficult to synthesize reliably.

Briefly, as described by Sieving et al. in *Bioconjugate Chem.* 1, 65–71 (1990), the standard procedure for the synthesis of poly(1-lysine-Gd.DTPA) involves coupling of DTPA to the preformed poly(1-lysine) polypeptide followed by incorporation of the gadolinium ion (in the form of a salt, such as $GdCl_3$) into the poly(1-lysine-DTPA) intermediate. However, this method of preparing poly(1-lysine-DTPA) suffers from variable conjugation efficiency, which is preferably >90% lysine repeat units functionalized with DTPA, and requires an extended purification procedure to remove by-products.

Furthermore, the current synthetic methodology for poly(1-lysine.DTPA) calls for the monoactivation of DTPA by conversion to a carboxy anhydride reactive intermediate, where multiactivation of DTPA can lead to poly(1-lysine) crosslinking and consequently to a loss in imaging selectivity. Also, as previously stated, the by-products of the DTPA poly(1-lysine) coupling reaction require a lengthy and tedious separation, resulting in a poorer product yield.

Related co-pending commonly owned U.S. patent applications Ser. No. 10/609,269 filed Jun. 26, 2003 and 10/209,726 filed Jul. 31, 2002 (published Feb. 5, 2004 under Publication No. US 2004/0022857) disclose efficient means of preparing extended poly(amino acids) conjugated to chelator moieties that form coordination complexes with paramagnetic ions. The method involves the low temperature activation of $DTPA.5NEt_3$, wherein $NEt_3$ is triethylamine, with isobutylchlorofomate (IBCF) in order to maximize the amount of monoactivated DTPA produced. While this approach provides additional efficiencies based upon its use of lower temperatures relative to known methods, improved methods continue to be sought, especially in light of the challenges presented for synthesizing highly conjugated polymers.

BRIEF DESCRIPTION OF THE INVENTION

The present invention provides a novel and efficient method for the syntheses of extended poly(amino acids) conjugated to imaging agents, such as organic nitroxyl radicals, iodinated organic moieties, chelator moieties (DTPA, etc.), protected chelator moieties, and of MRI contrast-enhancing agents comprising such poly(amino acids) conjugated to chelator moieties complexed with paramagnetic ions. Unlike previous techniques, the amino acid is conjugated to the imaging agent at the monomer stage, leading to the formation of a poly(amino acid) backbone having 100% imaging agent conjugation upon polymerization if desired. Furthermore, this alternative synthetic route to the poly(amino acid-imaging agent) utilizes transition metal or inorganic/organic base-catalyzed ring opening polymerization of the cyclic Nε-(imaging agent)-Nα-carboxy-amino acid anhydride. The degree of conjugation of the polymer can be controlled by copolymerizing the Nε-(imaging agent)-Nα-carboxy-amino acid anhydride with the unconjugated monomer, Nα-carboxy-amino acid anhydride. The present method allows for the development of new hybrid polymeric agents by block, random, or mixed copolymerization of the Nε-imaging agent-Nα-carboxy-amino acid anhydride with other amino acid N-carboxy anhydrides (NCA) as well as strained cyclic organic and inorganic monomers. The present method provides for unexpectedly controllable and increased conjugation of the polymer.

The method can also be used for the copolymerization of the Nε-imaging agent-Nα-carboxy-(amino acid) anhydride with other amino acid N-carboxy anhydrides and their derivatives.

Therefore, in one aspect, the present invention relates to a method for preparing a polypeptide comprising monomer units (I), (II), and (III):

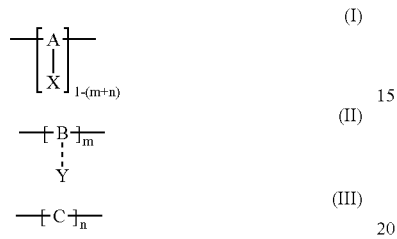

wherein said monomer units (I), (II), and (III) are randomly distributed or occurring together in said polypeptide;

wherein (A) is a first amino acid selected from the group consisting of lysine and ornithine, and (B) is a second amino acid which is the same as or different from (A); and (C) is a third amino acid different from both (A) and (B);

wherein (X) is an imaging agent conjugated to said first amino acid (A), wherein said imaging agent (X) is selected from the group consisting of organic nitroxyl radicals, iodinated organic moieties, chelator moieties, and protected chelator moieties;

wherein said imaging agent (X) is optionally complexed with a paramagnetic cation or a radioactive cation when said selected imaging agent is a chelator moiety;

wherein said imaging agent (X) is optionally conjugated to said first amino acid (A) through a linking group selected from the group consisting of $C_1$ to $C_{20}$ aryl, heteroaryl, linear, branched or cyclic alkyl groups, wherein one or more $CH_2$ may be fully or partly substituted with —S—, —O—, —N—, —CH=CH—, aryl, heteroaryl, linear, branched or cyclic alkyl or —C≡C—, or combination thereof;

wherein said second amino acid (B) is optionally covalently bonded to a pendant (pre)targeting moiety (Y);

wherein m is the mole fraction of said monomer units (II) having a numeral value ranging from 0 to about 0.99; and n is the mole fraction of said monomer units (III) having a numeral value ranging from 0 to about 0.99, wherein n>0 only when m>0 , wherein the sum of m+n≦0.99; and wherein 1−(m+n) is the mole fraction of said monomer units (I);

said method comprising the steps of
(a) providing said first amino acid (A) conjugated to said imaging agent (X); and when m>0 providing said second amino acid (B) optionally bonded to said pendant (pre)targeting moiety (Y); and when n>0 providing said third amino acid (C);
(b) contacting said first amino acid (A) conjugated to said imaging agent (X) with phosgene or triphosgene to form the N-carboxyanhydride of said first amino acid (A) conjugated to said imaging agent (X), and when m>0, contacting said second amino acid (B) optionally bonded to said pendant (pre)targeting moiety (Y) with phosgene or triphosgene to form the N-carboxyanhydride of said second amino acid (B) optionally bonded to said pendant (pre)targeting moiety (Y); and when n>0, contacting said third amino acid (C) with phosgene or triphosgene to form the N-carboxyanhydride of said third amino acid (C); and
(c) forming said polypeptide
  (i) when m+n=0, by polymerizing said N-carboxyanhydride of said first amino acid (A) conjugated to said imaging agent (X) to form said polypeptide, wherein said polypeptide is a homopolymer having monomer units (I); but
  (ii) when m>0 and n=0,
    (iia) by polymerizing said N-carboxyanhydride of said first amino acid (A) conjugated to said imaging agent (X) to form monomer units (I) occurring together, and polymerizing said N-carboxyanhydride of said second amino acid (B) optionally bonded to said pendant (pre)targeting moiety (Y) to form monomer units (II) occurring together, followed by the polymerization of monomer units (I) with monomer units (II) to form said polypeptide, wherein said polypeptide is a block polymer; or
    (iib) by simultaneously polymerizing said N-carboxyanhydride of said first amino acid (A) conjugated to said imaging agent (X) with said N-carboxyanhydride of said second amino acid (B) optionally bonded to said pendant (pre)targeting moiety (Y) to form said polypeptide, wherein said monomer units (I) and (II) are randomly distributed, and wherein said polypeptide is a random copolymer; but
  (iii) when m>0 and n>0,
    (iiia) by polymerizing said N-carboxyanhydride of said first amino acid (A) conjugated to said imaging agent (X) to form monomer units (I) occurring together, and polymerizing said N-carboxyanhydride of said second amino acid (B) optionally bonded to said pendant (pre)targeting moiety (Y) to form monomer units (II) occurring together, and polymerizing said N-carboxyanhydride of said third amino acid (C) to form monomer units (III) occurring together, followed by the polymerization of monomer units (I) with monomer units (II) and (III) to form said polypeptide; and wherein said polypeptide is a block polymer; or
    (iiib) by simultaneously polymerizing said N-carboxyanhydride of said first amino acid (A) conjugated to said imaging agent (X) with said N-carboxyanhydride of said second amino acid (B) optionally bonded to said pendant (pre)targeting moiety (Y) and with said N-carboxyanhydride of said third amino acid (C) to form said polypeptide, wherein said monomer units (I), (II), and (III) are randomly distributed, and wherein said polypeptide is a random copolymer; or
    (iiic) by polymerizing one of said N-carboxyanhydride of said first amino acid (A) conjugated to said imaging agent (X) or said N-carboxyanhydride of said second amino acid (B) optionally bonded to said pendant (pre)targeting moiety (Y) or said N-carboxyanhydride of said third amino acid (C) to form monomer units (I), (II), or (III) occurring together, followed by the simultaneous polymerization of said monomer units (I), (II), or (III) occurring together with whichever two of said N-carboxyanhydride of said first amino acid (A) conjugated to said imaging agent (X) or said N-carboxyanhydride of said second amino acid (B) optionally bonded to said pendant (pre)targeting moiety (Y) or said N-carboxyanhydride of said third amino acid (C) remain after formation of said monomer units (I), (II), or (III) occurring together, to form said polypeptide, wherein said polypeptide is a mixed copolymer comprising monomer units (II) and (III) randomly distributed between said monomer units (I) occurring together or is a mixed copolymer comprising monomer units (I) and (III) randomly distributed between said monomer units (II) occurring together, or is a mixed copolymer comprising monomer units (I) and (II) randomly distributed between said monomer units (III) occurring together.

In another aspect, the present invention relates to a method of preparing a polypeptide comprising monomer units (I) and (II):

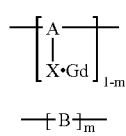

(I)

(II)

wherein said monomer units (I) and (II) are randomly distributed or occurring together in said polypeptide;

wherein (A) and (B) are both lysine; (X) is DTPA; (X.Gd) is DTPA complexed with gadolinium (III); m is the mole fraction of monomer units (II) having a value ranging from 0 to about 0.99; and 1-m is the mole fraction of monomer units (I);

(a) providing said lysine (A) conjugated to said DTPA (X) complexed with said gadolinium (III) (Gd), and when m>0 providing said lysine (B);
(b) contacting said lysine (A) conjugated to said DTPA (X) complexed with gadolinium (III) (Gd) with phosgene or triphosgene to form the N-carboxyanhydride of said lysine (A) conjugated to said DTPA (X) complexed with gadolinium (III) (Gd), and when m>0, contacting said lysine (B) with phosgene or triphosgene to form the N-carboxyanhydride of said lysine (B); and
(c) when m=0, polymerizing said N-carboxyanhydride of said lysine (A) conjugated to said DTPA (X) complexed with gadolinium (III) (Gd) to form said polypeptide, wherein said polypeptide is a homopolymer having monomer units (I),
but when m>0 polymerizing said N-carboxyanhydride of said lysine (A) conjugated to said DTPA (X) complexed with gadolinium (III) (Gd) to form monomer units (I) occurring together, and polymerizing said N-carboxyanhydride of said lysine (B) to form monomer units (II) occurring together, followed by the polymerization of monomer units (I) with monomer units (II) to form said polypeptide, wherein said monomer units (I) and (II) each occur together, and wherein said polypeptide is a block polymer or when m>0, simultaneously polymerizing said N-carboxyanhydride of said lysine (A) conjugated to said DTPA (X) complexed with gadolinium (III) (Gd) with said N-carboxyanhydride of said lysine (B) to form said polypeptide, wherein said monomer units (I) and (II) are randomly distributed, and wherein said polypeptide is a random copolymer.

In yet another aspect, the present invention relates to N-carboxyanhydride (NCA) salt of lysine bonded to diethylenetriamine-pentaacetic acid (DTPA), wherein the DTPA is complexed with gadolinium (III), and D is a cation from a physiologically acceptable non-toxic salt. The NCA salt is referred to as NCA-lysine—DTPA.Gd.D, and has the following structural formula

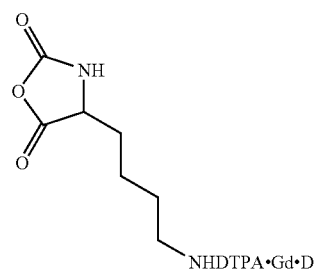

NHDTPA•Gd•D

Examples of suitable cations D include, but are not limited to $H^+$, $Na^+$ (from sodium bicarbonate ($NaHCO_3$) or sodium citrate ($Na_3Cit$) [i.e., ($NaO_2CCH_2C(OH)(CO_2Na)CH_2CO_2Na$)], $K^+$ (from potassium phosphate ($K_2HPO_4$)), and $NEt_3H^+$ (from the triethylamine hydrochloride ($NEt_3HCl$)).

In yet another aspect, the present invention relates to an N-carboxyanhydride (NCA) of lysine bonded to 1,4,7,10-tetraazacyclododecane-N,N',N'',N'''-tetraacetic acid (DOTA), wherein the DOTA is complexed with gadolinium (III). The compound is referred to as NCA-lysine—DOTA.Gd and has the following structural formula

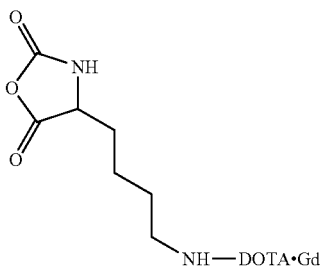

NH—DOTA•Gd

DETAILED DESCRIPTION OF THE INVENTION

The present invention provides a new method to synthesize polypeptide imaging agent materials, also referred to herein as "poly(amino acid-imaging agent)" materials with an unexpectedly high range of imaging agent conjugation and purity. The degree of conjugation can be controlled by copolymerizing the Nε-imaging agent-Nα-carboxy-(amino acid) anhydride with an unconjugated monomer, Nα-carboxy-(amino acid) anhydride at the correct stoichiometry. The poly(amino acid-imaging agent) product can be obtained in high purity without a rigorous purification since all impurities are removed at the monomer synthesis stage. The method also prevents formation of polypeptide crosslinks, which can lead to poorer agent issue selectivity. In addition, this method allows for homopolymerization and random, block, or mixed copolymerization of the imaging agent-functionalized amino acid repeat unit with other monomers which are also susceptible to the same ring opening polymerization chemistry, such as the corresponding NCA of other amino acids. Finally, the method of polymerization can be utilized with various imaging agents, but typically DTPA, DOTA or EDTA, where the corresponding NCA-imaging agent monomer can then be converted to an appropriate polypeptide.

Unless otherwise indicated, the reactants and reagents used in the reactions described below are readily available materials. Such materials can be conveniently prepared in accordance with conventional preparatory procedures or obtained from commercial sources.

In the present disclosure, the terms "poly(amino acid)" and "polypeptide" are used interchangeably. The term "contrast-enhancing agent" is sometimes abbreviated to "contrast agent." The terms "conjugation" or "conjugated," mean that and amino acid residue of the poly(amino acid) chain in attached covalently, i.e., chemically bonded, with at least a portion of another organic molecule, which may be the imaging agent or chelator for a cation. Thus, the process of conjugation also includes a process of substitution of at least one atom of an amino acid with a portion of the imaging agent. The term "residue", as used in this disclosure, means the portion of a compound attached to another compound or the remaining portion of a monomeric unit that is linked with portions of other monomeric units to form the polymer. As used herein with respect to amino acids, "α", "Nα", and "α-N" are interchangeable and refer to the amine group (—NH$_2$) attached to the carbon atom next to the carboxyl group (—COOH), and "ε", "Nε", and "ε-N" refer to the terminating amine group (—NH$_2$) opposite the end where the a amine group is located. "Monomer" refers either to a low molecule weight compound capable of being polymerized with itself or other similar compounds and also refers to the corresponding monomer moiety, such as to each of monomer units (I), (II), or (III), that is contained in the polymeric chain.

Products of the present method include homo-poly(amino acid) chains comprising monomer units (I), wherein the amino acid (A) of monomer units (I) is conjugated to an imaging agent (X). Other products include random, block, and mixed copolymers comprising monomer units (I) and monomer units (II) and optionally monomer units (III). In may instances, the imaging agent (X) will be complexed with a paramagnetic cation for use as a CT or MRI contrast-enhancing agent or complexed with a radioactive cation for use in SPECT or PET nuclear medicine. Monomer units (II) comprise a second amino acid (B), which may be the same as, or different from first amino acid (A). Monomer units (III) comprise a third amino acid (C), which differs from both amino acid (A) and amino acid (B).

Suitable amino acids for use as first amino acid (A) include lysine and ornithine. When present, second amino acid (B) may be lysine, ornithine, alanine, arginine, asparagine, aspartic acid, cysteine, glutamine, glutamic acid, glycine, histidine, isoleucine, leucine, methionine, phenylalanine, proline, serine, threonine, tryptophan, tyrosine, and valine. When third amino acid (C) is present, it is independently selected from any of the aforementioned amino acids, except that it can not be the same as amino acid (A) or amino acid (B). Unless indicated otherwise, each amino acid referred to herein may be present in the form of any of its stereoisomers. For example, "lysine" may be d-lysine, l-lysine or dl-lysine. Furthermore, dl-lysine refers to any mixture of the d and l-stereoisomers. The same holds true for the other amino acids referred to herein.

Optionally, imaging agent (X) may be conjugated to the first amino acid (A) through a linking group. As used herein, the term "linking groups" refers to $C_1$ to $C_{20}$ aryl, heteroaryl, linear, branched or cyclic alkyl groups, wherein one or more $CH_2$ may be fully or partly substituted with —S—, —O—, —N—, —CH=CH—, aryl, heteroaryl, linear, branched or cyclic alkyl or —C≡C—, or combination thereof, e.g., SCN.

Furthermore, a pendant (pre)targeting moiety (Y) may optionally be covalently bonded to second amino acid (B), when present. The dashed lines shown in monomer units (II) above indicated that pendant (pre)targeting moiety (Y) may or may not be present, i.e. chemical bonding with second amino acid (B) is optional. Typically, (Y) is used for targeted imaging of a biological marker such as cell surface receptors. Examples of optional pendant (pre)targeting moieties (Y) include, but are not limited to, biotin, galactose, glucose, estrogens, folate, folic acid, cobalamine, mannitol, mannose, peptides, PNAs (peptide nucleic acids), aptamers, and small organic molecules used in disease therapies, e.g., doxorubicin, taxol, letrozole, dexamethasone, 5-fluororacil, paclitaxel, tamoxifen, exemestane, farestone, zoladex, faslodex, camptothecin, and the like. In practice, some such targeted moieties could bind to cell surface receptors and may undergo endocytosis to also allow concentration of the imaging agent within the target cells. Alternatively, the targeted polymer would remain bound to the cell surface receptor and not be internalized. In a third (pre)targeting mechanism, a bifunctional antibody, which can bind to a biomarker, is introduced into the subject and allowed to accumulate at the biomarker of interest. The polymeric agent, targeted for the second free binding site of the antibody, is then introduced and accumulates at the biomarker upon binding to the antibody.

The (pre)targeting moiety (Y) may be attached to the second amino acid (B) by the methods described by Tsai et al. in *Bioconjugate Chem.* 12, 264–270 (2001) and by Wilbur et al. in *Bioconjugate Chem.* 9, 813–825 (1998). Typically, the (pre)targeting moiety (Y) is covalently bonded to the second amino acid (B) by activation of a functional group within the (pre)targeting moiety (Y) to permit attachment to amino acid (B). Alternatively, a functional group within the amino acid (B) may be activated to permit attachment to the (pre)targeting moiety (Y). As another alternative, two naturally occurring functional groups of the amino acid (B) and pretargeting moiety (Y) may react to produce the protected B—Y. This step is followed by removal of protecting groups of the product B—Y and conversion to the corresponding NCA of B—Y.

For example, when the pendant (pre)targeting moiety (Y) is biotin, and the second amino (B) acid is lysine, biotin may be attached to lysine through activation of the single biotin carboxylate group by 1,3-dicyclohexylcarbodiimide/N-hydroxysuccinimidyl (DCC/NHS) conversion to the succinimidyl ester, followed by mixing with one equivalent of Nα-BOC-lysine-methylester, wherein N-tert-butoxycarbonyl (BOC) is a protecting group. The biotin is coupled to the free Nε amine to provide the protected conjugate Nα-BOC-lysine-methyl ester-Nε-biotin. BOC deprotection via an acid and deesterfication provide lysine-Nε-biotin for conversion to the corresponding NCA.

The relative amounts of monomer units (I), (II), and (III) in the polypeptide imaging agents of the present invention may be represented as mole fractions, where the mole fraction of (II) is given by m; the mole fraction of (III) is given by n; and the mole fraction of monomer units (I) is 1−(m+n). The numerical values of m and n each independently range from 0 to 0.99, and the sum of m and n is less than or equal to 0.99. However, n>0 only when m>0. Thus, in the copolymers, m may be >0 and n may be 0, or both m and n may be >0, but the sum of m+n is always less than or equal to 0.99.

Thus, the polypeptides prepared by the method of the present invention include homopolymers containing only monomer units (I), wherein m and n are both 0, as well as copolymers comprising monomer units (I), as well as monomer units (II) and optionally (III). Furthermore, in the copolymers, the monomer units (I) and (II) and optional (III) may be randomly dispersed throughout the polymer chain. In the random polypeptides the relative mole fractions of the monomer units contained therein may vary widely depending on the application and the properties desired. Alternatively, the copolymers may be block polymers, which refers to a polymer made up of sections or blocks of monomer units (I) occurring together, and sections or blocks of monomer units (II) and optionally sections or blocks of monomer units (III). As another alternative, the copolymers may be mixed copolymers, which refers to a polymer made up of block oligomers comprising monomer units (I), (II), or (III) occurring together, while the other two monomers (I) and (II) or (II) and (III) or (I) and (III) are randomly dispersed between the block oligomer units.

The sum of monomer units (I), (II), and (III) in the polypeptides prepared by the present method is an integer ranging from 2 to 2000, but preferably ranges from about 50 to about 1500, and more preferably ranges from about 100 to about 400.

All polypeptides prepared by the present method comprise monomer units (I). Therefore, the common initial reactant for all polypeptides of the present method is an amino acid (A) capable of reacting and combining with the imaging agent (X).

Initially, the present method comprises providing the first amino acid (A), such as lysine or ornithine, conjugated to an imaging agent (X) at the Nε of amino acid (A). A wide variety of imaging agents (X) is suitable for bonding with the ε amine of the amino acid. For example, (X) may be a chelator moiety, a protected chelator moiety, an iodinated organic species, or a stable organic nitroxyl radical. Furthermore, when the imaging agent (X) is a chelator moiety, the chelator moiety may be complexed with a cation, such as a paramagnetic cation or a radioactive cation. As used herein, the terms "chelating agent", "chelator", and "chelator moiety", are interchangeable. Furthermore, the term "imaging agent" includes not only compounds, such as those listed herein, but also the residue attached to the ε-amine of the α-amino acid (A).

Suitable stable organic nitroxyl radicals include, but are not limited to, 2,2,6,6-tetramethyl-1-piperidinyloxy (TEMPO), 4-hydroxy-2,2,6,6-tetramethyl-1-piperidinyloxy (4-OH-TEMPO), and 4-amino-2,2,6,6-tetramethyl-1-piperidinyloxy (4-NH$_2$-TEMPO).

Examples of iodinated organic species include, but are not limited to, iohexol (N,N'-Bis(2,3-dihydroxypropyl)-5-[N-(2,3-dihydroxypropyl)-acetamido]-2,4,6-triiodoisophthalamide) and iodixanol (5,5'-[(2-hydroxy-1,3-propanediyl)bis(acetylimino)]bis[N,N'-bis(2,3-dihydroxypropyl)-2,4,6-triiodo-1,3-benzenedicarboxamide]). Iohexol is commercially available as OMNIPAQUE™, and iodixanol is commercially available as VISIPAQUE™. Such species are useful as contrast agents for CT scans (computed tomography imaging).

Examples of chelator moieties include, but are not limited to, diethylenetriamine-pentaacetic acid (DTPA), triethylenetraminehexaacetic acid (TTHA), ethylenediaminetetraacetic acid (EDTA), 1,2-diaminocyclohexane-N,N,N',N'-tetraacetic acid, N,N'-di-(2-hydroxybenzyl)ethylenediamine (HBED), N-(2-hydroxyethyl)ethylenediaminetriacetic acid, nitrilotriacetic acid, ethylene-bis(oxyethylenenitrilo)tetraacetic acid (EGTA), 1,4,7,10-tetraazacyclododecane-N,N',N'',N'''-tetraacetic acid (DOTA), 1,4,7,10-tetraazacyclododecane-N,N',N''-triacetic acid (DO3A), 1,4,7-tris(carboxymethyl)-10-(2'-hydroxy)propyl)-1,4,7,10-tetraazocyclododecane (HP-DO3A), 1,4,7-triazacyclonane-N,N',N-triacetic acid (NOTA), or 1,4,8,11-tetraazacyclotetradecane-N,N',N'',N'''-tetraacetic acid (TETA). However, DTPA, EDTA, and DOTA are the most commonly used chelating agents for conjugating to the amino acid. Examples of protected chelator moieties include but are not limited to DTPA permethyl ester, DOTA permethyl ester, and other chelators containing arylated or alkylated esters, wherein the alkyl groups are selected from methyl, ethyl, propyl, butyl, pentyl, hexyl, t-butyl, benzyl, perfluoroalkyl and the like, and wherein the alkyl units may be straight chained, branched or cyclic where relevant, and the like, and wherein the aryl groups are selected from benzene, toluene, nitrobenzene fluorobenzenes and the like.

Other suitable chelator moieties include those having formulae (IV), (V), (VI), or (VII), wherein each R is independently selected from the group consisting of $C_1$ to $C_{20}$ aryl, heteroaryl, linear, branched or cyclic alkyl groups. However, when R is an alkyl group, one or more $CH_2$ may be fully or partly substituted with —S—, —O—, —N—, —CH=CH—, aryl, heteroaryl, linear, branched or cyclic alkyl or —C≡C—, or combination thereof.

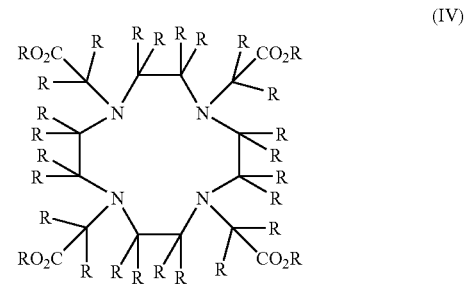

(IV)

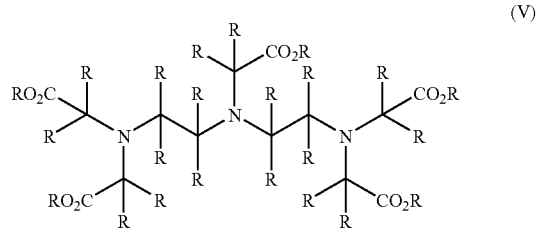

(V)

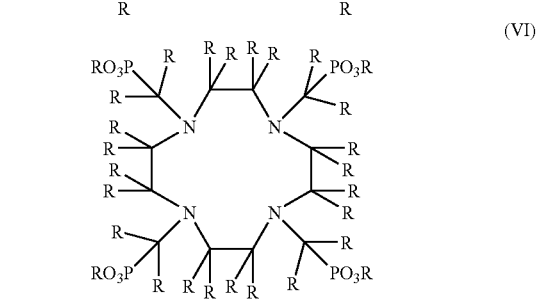

(VI)

-continued

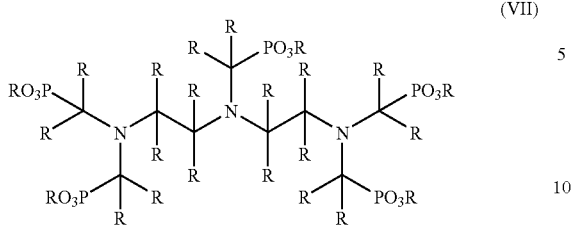

(VII)

Suitable paramagnetic cations for complexing with the chelator moiety include, but are not limited to gadolinium (III), dysprosium (III), holmium (III), europium (III), iron (III), or manganese (II). Suitable radioactive cations include, but are not limited to copper (II), indium (II), indium (III), and yttrium (III).

The imaging agent (X) may be attached to the ε-amine of the amino acid using conventional techniques. For example, the α-amine of the first amino acid (A) may initially be coupled with a boron-containing compound to form an organic soluble borate-protected amino acid intermediate. The ε-amine of the amino acid (A) sidechain is then free to undergo a subsequent reaction with imaging agent (X). Suitable boron-containing compounds include 9-borobicyclononane (9-BBN) and general boranes, such as tributylborane, as well as borates, boronamides, and boronic acids. The reduction reaction between the amino acid and the boron-containing compound may be carried out under the conditions described by Dent, III et al. where 9-BBN was used as the protecting group (*Org. Lett.* 4 (8), 1249–51 (2002)). The reaction is carried out by first dissolving the boron-containing compound in a polar solvent, such as methanol, acetone, dioxane, tetrahydrofuran (THF), or dimethylformamide (DMF), and heating to reflux, typically at a temperature ranging from about 10° C. to about 160° C., in an inert atmosphere, such as nitrogen gas. The amino acid (A) is then added to the solution, and the mixture heated to reflux again (typically from about 10° C. to about 160° C.) until the amino acid sample is dissolved. The resulting borate-protected amino acid complex is organic-soluble, whereas amino acids alone are soluble only in water. The reaction is illustrated in Scheme 1:

Scheme 1

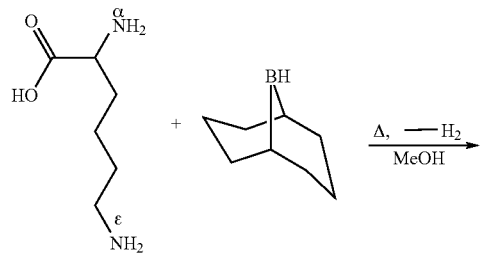

-continued

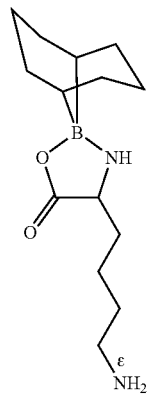

wherein the amino acid (A) is 1-lysine 1, and the boron-containing compound is 9-borobicyclononane (9-BBN) 2. The 9-BBN-lysine intermediate 3 produced comprises 9-BBN with the Nε-amino lysine side chain, which is free to undergo a further reaction with an imaging agent (X).

An imaging agent (X), such as one of those previously listed, may then be condensed with the borate-protected amino acid intermediate to form the borate-protected amino acid (A) conjugated with the imaging agent (X) at the Nε. Initially, the penta anion of the imaging agent may be prepared by the method described by Sieving et al. in *Bioconjugate Chem.* 1(1), 65–71 (1990). Briefly, in an inert atmosphere, the imaging agent is reacted with a tertiary amine, such as triethylamine (NEt₃), trimethylamine, tributylamine, tripropylamine, pyridine, and the like, in a polar organic solvent, such as acetonitrile, or tetrahydrofuran (THF), for example. The resulting solution is then heated to reflux at a temperature ranging from about 60° C. to about 80° C., but preferably about 55° C., until the sample dissolves, which is generally about an hour. Isobutylchloroformate (IBCF) is then added to the solution to form the activated mixed anhydride of the imaging agent, followed by the addition of the borate-protected amino acid intermediate. The desired borate-protected amino acid (A) conjugated with the imaging moiety (X) is then produced.

After adding the imaging agent (X) to the ε-amine of the borate-protected amino acid, deprotection may be facilitated by the method described in the aforementioned article by Dent III et al. (*Org. Lett.* 4 (8) 1249–51 (2002)). Briefly, the protecting group may be removed from the amino acid by ion exchange with a diamine, such as ethylenediamine (EDA), propanediamine, cyclohexyl-1,2-diamine, and the like, typically in methanol. Alternatively, deprotection may be facilitated by contact with aqueous 0.1M HCl, in methanol either in an inert atmosphere or in air. The mixture is heated to reflux, typically at a temperature ranging from about 20° C. to about 80° C., but usually about 60° C., for a time ranging from about 1 to about 240 minutes, but generally about 10 minutes, resulting in the desired amino acid (A) conjugated with the imaging moiety (X). The addition of the imaging agent (X), followed by the deprotection of the amino acid (A) is illustrated in Scheme 2:

Scheme 2

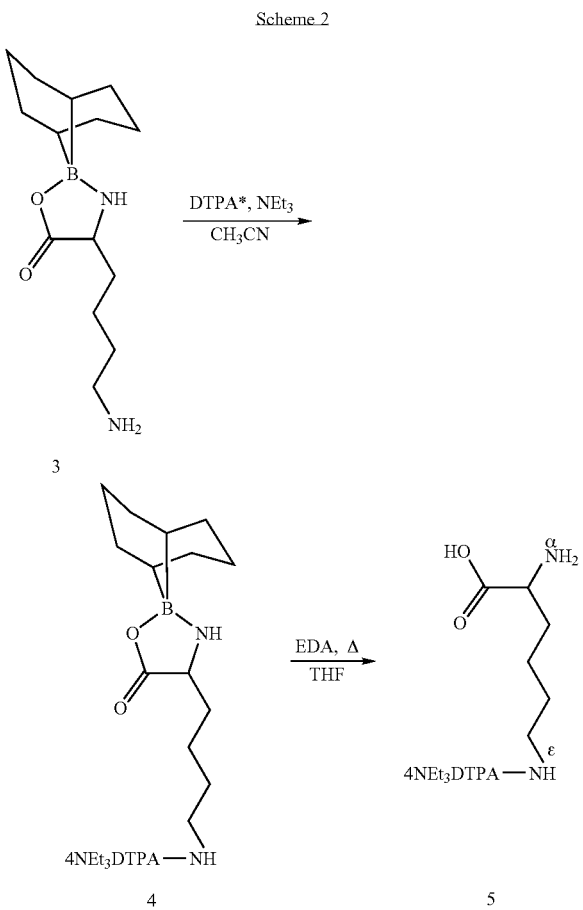

In Scheme 2, the 9-BBN-protected lysine intermediate 3 is reacted with activated DTPA* as the imaging agent (X) to form 9-BBN-lysine-DTPA 4, which is then deprotected using ethylene diamine (EDA) to form the desired lysine conjugated with DTPA 5. (The asterisk * indicates that it is the activated mixed anhydride of the chelator.)

In another embodiment, the Nε of the amino acid (A) may be conjugated with the imaging agent (X) without being protected by a boron-protecting group. The imaging agent is activated into its mixed anhydride form by reaction with a tertiary amine in a polar organic solvent, such as acetonitrile, in an inert atmosphere, as previously described, followed by the addition of isobutylchlorofomate (IBCF). The resulting slurry is then added to a solution comprising the amino acid and an organic base, such as N-methylmorpholine, for example. The desired amino acid (A) conjugated with the imaging agent (X) to the ε-amine, such as compound 5, is then isolated from the crude reaction mixture. An alternative method involves the reaction of DTPA* and Nα-protected lysine, wherein the protecting group (PG) may be N-tert-butoxycarbonyl (BOC), or fluorenylmethoxycarbonyl (FMOC), for example, to give PG-Nα-lysine-Nε-DTPA. The protecting group may then be removed upon addition of an acid to remove BOC or base to remove FMOC.

In another embodiment, a linking group, may be employed to conjugate the imaging agent (X) to the amino acid (A). As previously mentioned, such linking groups include $C_1$ to $C_{20}$ aryl, heteroaryl, linear, branched or cyclic alkyl groups, wherein one or more $CH_2$ may be fully or partly substituted with —S—, —O—, —N—, —CH=CH—, aryl, heteroaryl, linear, branched or cyclic alkyl, or —C≡C—, or combination thereof. Examples of such compounds include (lysine-SCN-DTPA) and (ornithine-SCN-DTPA), wherein (A) is lysine or ornithine, respectively; SCN is the linking group; and (X) is DTPA, and wherein the dash indicates covalent attachment. Attachment of the linking group may be accomplished using conventional synthetic techniques, as would be known by one of ordinary skill. One example for addition of a linking group includes mixing DTPA-benzyl isothiocyanate with PG-Nα-lysine to give PG-Nα-lysine-Nε-SCN-Bz-DTPA, wherein Bz is benzyl, and PG is a protecting group, such as BOC, FMOC, or one of the previously listed boron-containing compounds. The protecting group can then be removed, as previously described to provide lysine-Nε-SCN-Bz-DTPA. However, the invention is not limited to these compounds, and the employment of other suitable linking groups and imaging agents, as well as the method of attachment, would be obvious to one of ordinary skill.

MRI contrast-enhancing agents may be formed by complexing a chelator moiety, which is conjugated to amino acid (A), with a paramagnetic cation, such as one previously listed. In this embodiment, imaging agent (X) is the chelator moiety, and it is complexed with the paramagnetic cation. Alternatively, for other applications the chelator moiety may be complexed with a radioactive cation, such as one previously listed. Generally, the paramagnetic or radioactive cation enters the reaction in the form of a salt. The paramagnetic or radioactive cation is typically added prior to polymerization, but alternatively, the cation may also be added to the chelator moiety after polymerization. Furthermore, this step is optional, and the present method is not limited to forming the coordination complex between the paramagnetic or radioactive cation and the chelator moiety.

Labeling the amino acid (A) conjugated with the chelator moiety (X) with the paramagnetic cation or radioactive cation may be facilitated using a salt of the cation at a pH ranging preferably from about pH 5 to about pH 7. A gadolinium salt, such as gadolinium citrate, gadolinium chloride or other halide, gadolinium hydroxide, gadolinium oxide, or gadolinium acetate is typically preferred to provide gadolinium (III) as the paramagnetic ion. Typical salts of radioactive cations include halides, acetates, hydroxo- and oxo-salts. The reaction is typically conducted at a temperature ranging from about 10° C. to about 80° C. for about 2–24 hours.

When DTPA is the chelator moiety to be labeled with gadolinium (III), the reaction is run in the presence of a buffer, such as sodium bicarbonate ($NaHCO_3$), potassium phosphate ($K_2HPO_4$), sodium citrate ($Na_3Cit$) ($NaO_2CCH_2C(OH)(CO_2Na)CH_2CO_2Na$), or triethylamine hydrochloride ($NEt_3$·HCl), for example. The buffer, which is a physiologically acceptable non-toxic salt, provides a cation ($D^+$), which counters the overall negative (−1) charge of DTPA complexed with the paramagnetic cation. When sodium bicarbonate or sodium citrate is used as the buffer, the counterion ($D^+$) is $Na^+$. Potassium phosphate provides $K^+$, and triethylamine hydrochloride provides $NEt_3H^+$ as the cation $D^+$. However, as one of skill would know, the physiologically acceptable non-toxic salt (buffer) is not limited to those listed herein, and any organic solubilizing salt, such as 1,1,3,3-tetramethylguanidine, $(CH_3)_2N—C(=NH)—N(CH_3)_2$, as well as many others could be used to provide the $D^+$ counter cation.

Furthermore, as one of ordinary skill would know, the overall charge of the chelator moiety (X) complexed with the paramagnetic or radioactive cation determines whether a physiologically acceptable non-toxic salt is needed to counteract any negative ionic charge of the complex. For example when DOTA is the chelator moiety and gadolinium (III) is the paramagnetic cation, no buffer is needed because the (+3) positive charge of the paramagnetic cation counters the negative (−3) charge of DOTA. One of ordinary skill would know which chelator moieties complexed with a particular paramagnetic or radioactive cation would need a countercation to neutralize the charge.

Scheme 3 shows the reaction of lysine-DTPA 5 with gadolinium chloride (GdCl$_3$) in the presence of sodium citrate (Na$_3$Cit) to form the lysine-Nε-GdDTPA.Na complex 6, wherein Na$^+$ is the cation D.

Scheme 3

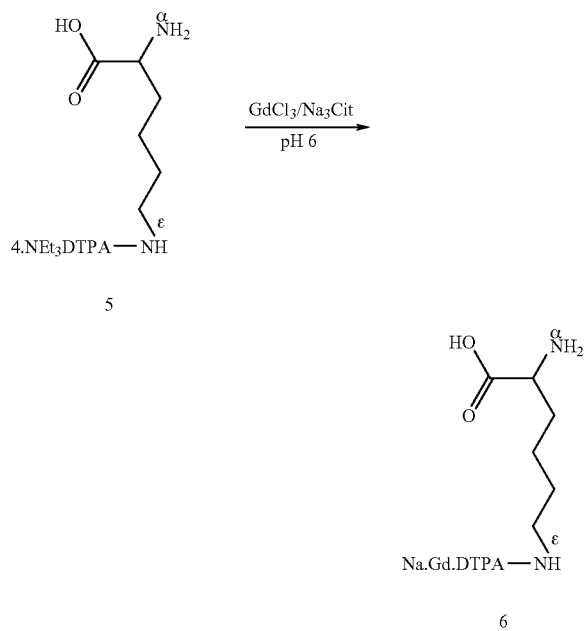

In the second step of the present method, the N-carboxyanhydride (NCA) of the amino acid (A) conjugated with the imaging agent (X) is then prepared, followed by ring-opening polymerization of the NCA monomer to form the desired homopolymer having monomer units (I), wherein there is 100% conjugation of the imaging agent.

However, conjugation may be controlled by preparing random, block, or mixed copolypeptides using the N-carboxyanhydride (NCA) of the amino acid (A) bearing the imaging agent (X) as one monomer (resulting in monomer units (I)), and at least one additional α-amino acid NCA comonomer of second amino acid (B) and optional third amino acid (C) (resulting in monomer units (II) and optionally (III)). As previously mentioned, second amino acid (B), may optionally be covalently bonded to a pendant (pre)targeting moiety (Y). Thus, the present method allows for the control of imaging agent (X) conjugation in the polymer chain, as well as control of the overall composition of the polymer chain.

In general, α-amino acid N-carboxyanhydride (NCA) monomers, also referred to as Leuchs' anhydrides, may be readily prepared by direct phosgenation using phosgene (carbonyl chloride, (COCl$_2$)) or triphosgene (hexachloromethylcarbonate, (OCCl$_3$)$_2$CO)), preferably under an inert atmosphere and non-hydrolytic conditions, as described by Hirschmann et al. in *JACS* 93 (11), 2746–2754 (1971). The phosgenation reaction is conducted in a polar organic solvent, such as tetrahydrofuran (THF), methylene chloride, dimethylformamide (DMF) or 1-methyl-2-pyrrolidinone (NMP), to reflux, typically at a temperature ranging from about 10° C. to about 80° C. for a time typically ranging from about 2 to about 24 hours. The procedure is applicable to form α-NCA monomers from the following α-amino acids: lysine, ornithine, alanine, arginine, asparagine, aspartic acid, cysteine, glutamine, glutamic acid, glycine, histidine, isoleucine, leucine, methionine, phenylalanine, proline, serine, threonine, tryptophan, tyrosine, and valine. Furthermore, the method is useful in forming the NCA of the amino acid (A) bearing the imaging agent (X), with or without the paramagnetic or radioactive cation. As previously mentioned, first amino acid (A) may be lysine or ornithine. Likewise, second amino acid (B) and third amino acid (C) may also be lysine or ornithine, as well as any of the other α-amino acids listed herein. However, third amino acid (C) must differ from both first amino acid (A) and second amino acid (B).

After formation of the α-NCA amino acid monomer(s), oligomerization or polymerization occurs via initiator/catalyst mediated ring opening of the NCA's. This allows control of the polymer chain-length, as well as the structure of the polypeptide. Furthermore, as previously mentioned, the degree of conjugation may be controlled by copolymerizing the NCA of the amino acid (A) bearing the imaging agent (X) with an unconjugated NCA amino acid monomer. Thus, homopolymers comprising monomer units (I), i.e. amino acid (A) bearing the imaging agent (X) may be formed (100% conjugation), as well as copolymers having any desired conjugation, wherein the copolymers comprise monomer units (I) and (II), i.e. amino acid (B) with or without (Y), and optionally (III), i.e., amino acid (C). In addition, new hybrid polymeric agents can be developed by block or random copolymerization of the NCA of the amino acid (A) bearing the imaging agent (X) with any of the other amino acid NCA's previously listed to form monomer units (II) and optionally (III).

One exemplary homopolymer having 100% contrast agent conjugation is poly(lysine-DTPA.Gd), wherein (A) is lysine; (X) is DTPA; and wherein DTPA has been complexed with gadolinium ion (Gd). An exemplary copolymer, wherein m>0, and n=0, is poly(lysine-DTPA.Gd)-(lysine-folate), wherein (A) is lysine; (X) is DTPA; and (B) is lysine. In this embodiment DTPA has been complexed with the gadolinium ion (Gd), and second amino acid (B), lysine, is bonded to folate, which is a pendant (pre)targeting moiety (Y). In another polypeptide, there is no (pre)targeting moiety (Y), and the copolymer is poly(lysine-DTPA.Gd)-(lysine) As previously mentioned, the copolymers comprising monomers units (I) and (II) may be block or random. As used herein, the dash indicates covalent attachment, and parentheses are used to represent a monomer unit.

Another exemplary copolymer formed by the polymerization of the corresponding α-NCA amino acid monomers, wherein m>0 and n>0 is poly(lysine-DTPA.Gd)-(lysine-folate)-(glycine). In this copolymer, (A) is lysine; (B) is lysine; and (C) is glycine. In addition, (X) is DTPA, which has been complexed to gadolinium ion (Gd), and lysine (B), is bonded to folate, i.e. (pre)targeting moiety (Y). The corresponding copolymer without (pre)targeting moiety (Y) is thus, poly(lysine-DTPA.Gd)-(lysine)-(glycine). These copolymers may be block, random or mixed.

As used herein, and as would be understood by the person of skill in the medical art, to which the invention pertains, the recitation of the polypeptides prepared by the present method also includes their salts, which are prepared by the addition of a physiologically acceptable non-toxic salt, as previously described with respect to DTPA.Gd.

In mixed copolymers, m>0 and n>0, and single monomer units are randomly distributed between blocks of another monomer unit. For example, in poly(lysine-DTPA.Gd)-(lysine-folate)-(glycine), monomers units (I) comprising (lysine-DTPA.Gd), may be polymerized into blocks. Monomer units (II) (lysine-folate) and monomer units (III) (glycine) may then be randomly distributed between the blocks of monomer (I) units. Alternatively, monomer units (II) could be polymerized to form blocks, and monomer units (I) and (III) could be randomly distributed between blocks of (II). Likewise, monomer units (III) could be polymerized into blocks, and monomer units (I) and (II) could be randomly distributed between the blocks of (III).

From the examples presented herein, it is clear that the present method may be extended to synthesize a very large number and wide variety of polypeptide imaging agents. Unlike previous methods, the imaging agent conjugation, as well as the composition of such polypeptides, can unexpectedly be controlled. Thus, as one of skill would clearly know, the method of the present invention is not limited to preparing the particular polypeptide imaging agents discussed herein.

Polymerization of NCA's is described by Deming in *Nature* 390, 386–89 (1997) and *Macromolec.* 32, 4500–02 (1999), and U.S. Pat. No. 6,680,365, as well as by Okada et al. in *Proc. Japan Acad.* 73 (Ser. B), 205–09 (1997) and by Hideo et al. in JP 60-15425. Briefly, the polymerization occurs by ring opening of the anhydride using a polymerization initiator in an organic solvent, such as DMF, THF, dicholoromethane, acetonitrile, dimethyl sulfoxide, dioxane, or any mixture thereof, for example. Suitable polymerization initiators include alkali metal hydroxides, such as KOH or NaOH, alkali metal alkoxide initiators, alkali metal initiators of diols, amines, and transition metal initiators comprising low-valent metal complexes.

Suitable low valent transition metal initiators include, but are not limited to, bipyNi(COD), wherein bipy is 2,2'-bipyridyl, and COD is defined as 1,5-cyclooctadiene; and phosphine complexes of cobalt or iron, such as $(PMe_3)_4Co$ and $(PMe_3)_4Fe$, wherein Me is methyl. Many other suitable low valent transition metal initiators comprising a low valent transition metal and a Lewis Base donor ligand are listed in aforementioned U.S. Pat. No. 6,680,365 to Deming. Suitable alkali metal alkoxide initiators include, but are not limited to, linear primary alkali metal alkoxides such as sodium methoxide, potassium methoxide, sodium ethoxide, potassium ethoxide, sodium-tert-butoxide, potassium-tert-butoxide, sodium pentoxide, potassium pentoxide, and the like; cyclic alkali metal alkoxides, such sodium cyclohexoxide, potassium cyclohexoxide, sodium cyclopentoxide, potassium cyclopentoxide, and the like. Suitable alkali metal initiators of diols include, but are not limited to, sodium 1,2 propandioxide, potassium 1,2 propandioxide, sodium 1,2 butanedioxide, potassium 1,2 butanedioxide, sodium 1,2 pentandioxide, potassium 1,2 pentandioxide, and the like. Mixed linear, branched and cyclic variants of the alkali metal alkoxide initators and alkali metal initiators are also included. Suitable amines include, but are not limited to, pyridine; linear primary amines, such as ethylamine, propylamine, butylamine, pentylamine, n-hexylamine, and the like; cyclic amines, such as cyclopentylamine, cyclohexyl amine, and the like; secondary amines, such as diethylamine, dibutylamine, trimethylamine, and the like, as well as mixed versions thereof. Also suitable are diamines such as 1,2 diaminopropane, 1,2 diamino butane, 1,2 diaminopentane, 1,2 diaminohexane, and the like. Also suitable are the mixed, linear, and branched amine variants thereof.

Use of the polymerization initiator allows the controlled preparation of random polymers, block polymers, mixed polymers, and homopolymers through the mediated addition of the NCA monomers to the active polymer chain-ends. In particular, block polymers may be synthesized by the sequential addition of different α-amino acid-NCA monomers, such as those previously listed, to the initiator. Random polymers may be prepared by the simultaneous polymerization of different α-amino acid-NCA monomers. Mixed copolymers may be prepared by alternating the addition of one α-amino acid-NCA monomer (until a desired block oligomer is formed) with the addition of different α-amino acid-NCA monomers to the active polymer chain-ends. Scheme 4 depicts the formation of the poly(lysine-DTPA.Gd) 8 homopolymer from NCA monomer 7 comprising α-1-lysine-NCA conjugated with DTPA.Gd, followed by ring-opening polymerization using NaOH as the polymerization initiator:

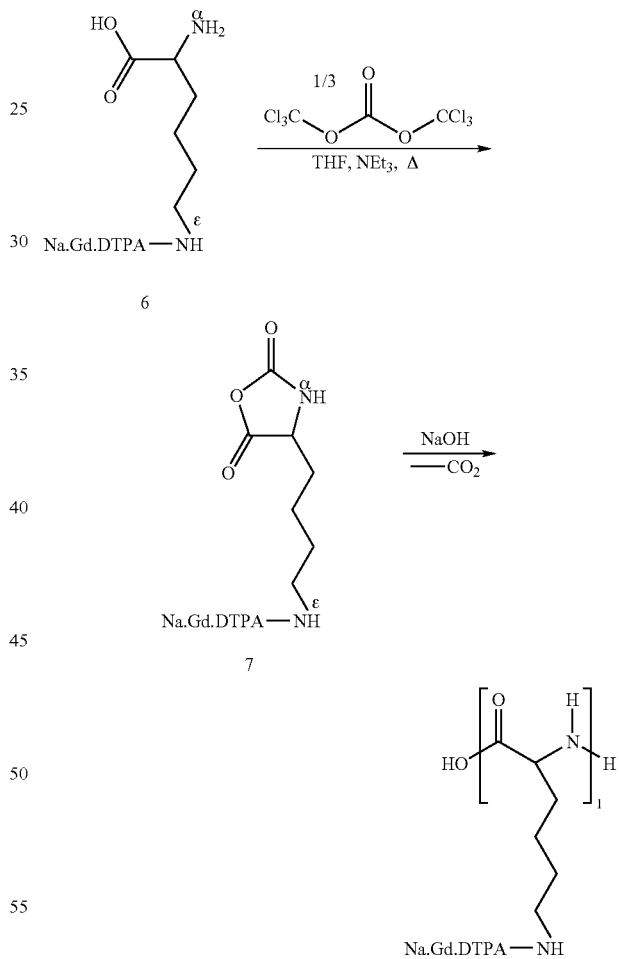

In polypeptide 8, subscript "l" indicates that the polymer is a homopolymer having 100% chelate conjugation. In this embodiment, weight average molecular weight ($M_w$) of these gadolinium-labeled homopolymers ranges from about 1400 g/mole to about 1,400,000 g/mol (corresponding to 2–2000 monomer units (I)), preferably from about 35,000 g/mol to about 1,050,000 g/mol (i.e. 50–1500 monomer units), and more preferably from about 70,000 g/mol to about 280,000 g/mol (i.e. 100–400 monomer units).

Another preferred polypeptide imaging agent that may be synthesized using the present method described herein is poly(lysine-DTPA.Gd)-(lysine), which may be a random or block copolymer. Poly(lysine-DTPA.Gd)-(lysine) may be prepared by the copolymerization of the first NCA monomer comprising α-1-lysine-NCA conjugated with DTPA.Gd with an unconjugated second NCA monomer comprising the α-1-lysine-NCA. In this embodiment, only monomers units (I) and (II) are present (m>0, and n=0). Typically, the value of m ranges from about 0.01 to about 0.99, but preferably the value of m ranges from about 0.1 to about 0.4, and more preferably the value of m ranges from about 0.2 to about 0.3. In monomer units (I) and (II), first and second amino acids (A) and (B) are both lysine; and imaging agent (X) is DTPA. Preferably, DTPA is complexed with a gadolinium paramagnetic cation.

The following Examples 1–5 illustrate the synthesis of the homopolymer poly(lysine-DTPA.Gd) 8, wherein 1-lysine is the α-amino acid (A) and DTPA is imaging agent (X). Furthermore, in the homopolymer, imaging agent (X) is complexed with the paramagnetic cation gadolinium (III) "PL" refers to poly(lysine). Example 6 is another example of the polymerization step. Example 7 illustrates the synthesis of a copolymer. However, it should be understood that other amino acids can also be used, as well as other chelating moieties and paramagnetic or radioactive ions. Furthermore, other imaging agents listed herein may be substituted in the reactions.

EXAMPLE 1

Synthesis of Lysine-Nε-DTPA 5

(A) Synthesis of 9-BBN-lysine complex, 3, depicted in Scheme 1.

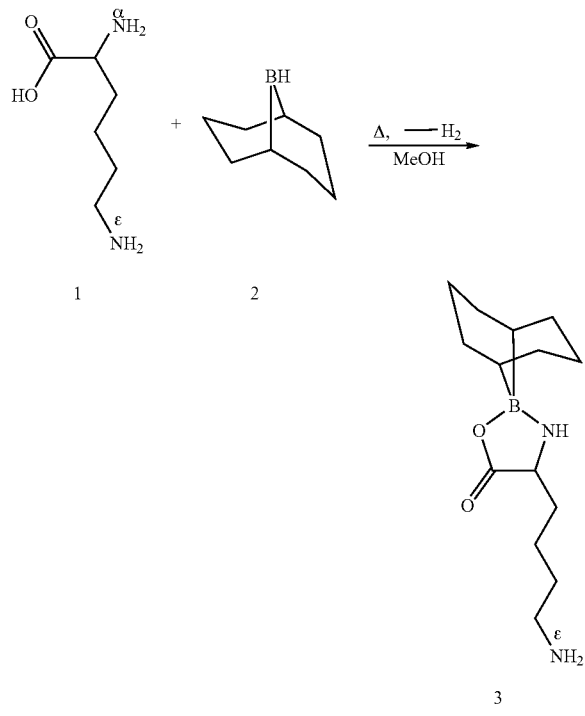

A sample of lysine, 1, (1 eq) is stirred in MeOH (0.03M solution) at ambient temperature. An aliquot of a solution of 9-borobicyclononane (9-BBN) (1 eq), 2, in tetrahydrofuran (THF) is introduced by syringe, and the cloudy reaction mixture is stirred under refluxing conditions (~50° C.) over 1 hour to give a clear colorless solution. The volatile organic solvents are removed under reduced pressure to give a solid that is then redissolved in warm (~40° C.) THF and filtered to provide a colorless solution. The solution is filtered and the volatiles are removed in vacuo to afford 9-BBN-lysine, 3, as an off white solid, which is then washed with pentanes, dried in vacuo and used without further purification.

(B) Synthesis of 9-BBN-lysine-DTPA, 4, depicted in Scheme 2.

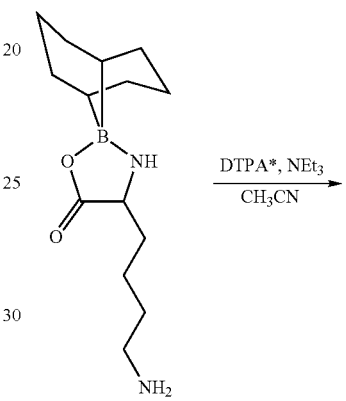

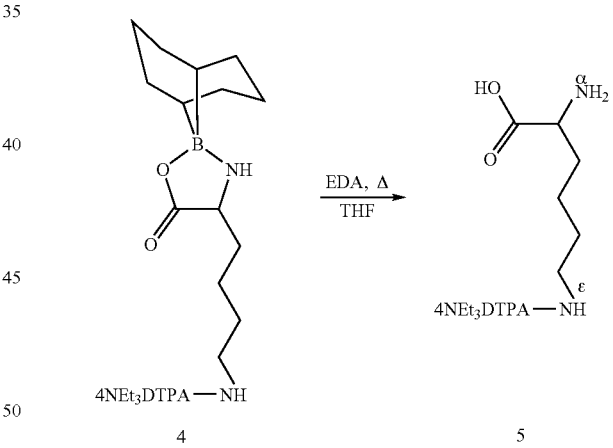

A sample of DTPA (1 eq) is added to a solution of acetonitrile (CH$_3$CN, 0.1 M), followed by the addition of triethylamine (NEt$_3$) (5 eq) to provide a cloudy solution that is then degassed for 20 minutes before stirring at 55° C. for 1 hour. The resulting clear colorless solution is then cooled to −45° C., followed by the dropwise addition of isobutylchlorofomate (IBCF) (1.1 eq) and stirring for 1 hour at −45° C., resulting in a white slurry. The slurry is then added to a CH$_3$CN solution of 9-BBN-lysine, 3, (1 eq), and the reaction mixture is stirred at ambient temperature for 12 hours. The volatiles are removed under reduced pressure and the residue recrystallized from THF/diethyl ether (Et$_2$O) to provide the 9-BBN-lysine-DTPA, 4, product as a white solid.

(C) Deprotection of 4 to Lysine-Nε-DTPA 5, Depicted in Scheme 2.

A THF solution of 4 (1 eq) is mixed with ethylene diamine (EDA) (1.1 eq) and heated to 60° C. for 10 mins. The volatile organic solvents are then removed by vacuum, and the residue washed with pentanes. The remaining residue is recrystallized from warm (~45° C.) THF/Et₂O to provide lysine-Nε-DTPA 5 as a white solid.

EXAMPLE 2

Alternate Synthesis of Lysine-Nε-DTPA 5

To a CH₃CN solution (0.1M) is added DTPA (1 eq) and triethylamine (NEt₃) (5 eq) to provide a cloudy solution that is then degassed for 20 mins before stirring at 55° C. for 1 hour. The resulting clear colorless solution is then cooled to −45° C. and isobutylchlorofomate (IBCF) (1.1 eq.) added dropwise over the course of about 20 minutes and stirred for 1 hour at −45° C. to give a white slurry. The slurry is then added to a clear dimethylformamide (DMF) solution of Nα-Boc-lysine (1 eq) and N-methylmorpholine (2 eq) followed by stirring at ambient temperature for 12 hours. The reaction mixture is then treated with acetylchloride (9 eq) in MeOH (0.1M) for 6 hours at ambient temperature at which point the volatiles are removed to afford a residue that is treated with NaOH (6 eq) in MeOH (0.1M) for 6 hrs. The volatiles are removed in vacuo and the resulting residue is purified by reversed phase silica gel chromatography to isolate lysine-Nε-DTPA 5 as a colorless solid.

EXAMPLE 3

Synthesis of Lysine-Nε-DTPA.Gd.Na 6, Depicted in Scheme 3

A sample of lysine-Nε-DTPA 5 (1 eq) from Example 1 or Example 2 is dissolved in H₂O to form a 0.1M solution, which is added to a pH 6 buffer solution of GdCl₃ (1.2 eq) and trisodium citrate (2.4 eq). The reaction mixture is stirred for 12 hours, the volume reduced under centrifugal vacuum and then twice passed through a Sephadex plug. The volume is reduced under centrifugal vacuum and then the reaction mixture is added to acetone (5 eq by volume). A white solid containing the product, lysine-Nε-DTPAGd.Na 6 precipitates, and the product 6 is isolated by filtration, followed by washing with acetone (3×10 mL) and drying in vacuo.

Scheme 3

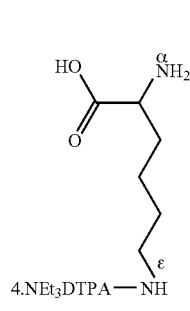

5

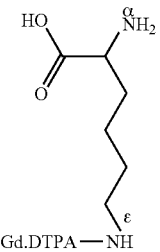

6

EXAMPLE 4

Synthesis of N-Carboxy Anhydride (NCA)-lysine-Nε-DTPA.Gd.Na 7, Depicted in Scheme 4

To a methylene chloride (CH₂Cl₂) solution (0.1M) of lysine-Nε-DTPA.Gd.Na, 6, (1 eq) from Example 3 and triethylamine (NEt₃) (2 eq) is added triphosgene (0.3 eq) at 0° C. The reaction mixture is stirred at ambient temp for 1 hour and then the volatile organic solvents removed in vacuo. The residue is extracted with ethyl acetate (EtOAc), filtered, and the volatiles removed to afford crude, 4, which is then recrystallized from CH₂Cl₂/pentanes to give NCA-lysine-Nε-DTPAGd.Na, 7, as a white solid.

Scheme 4

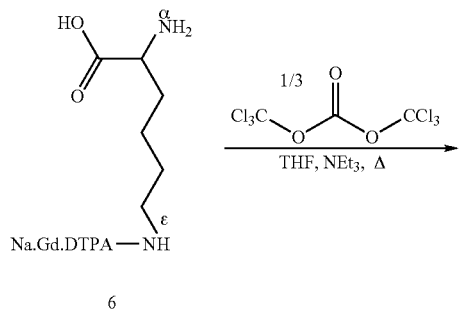

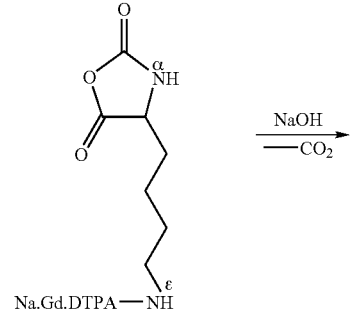

7

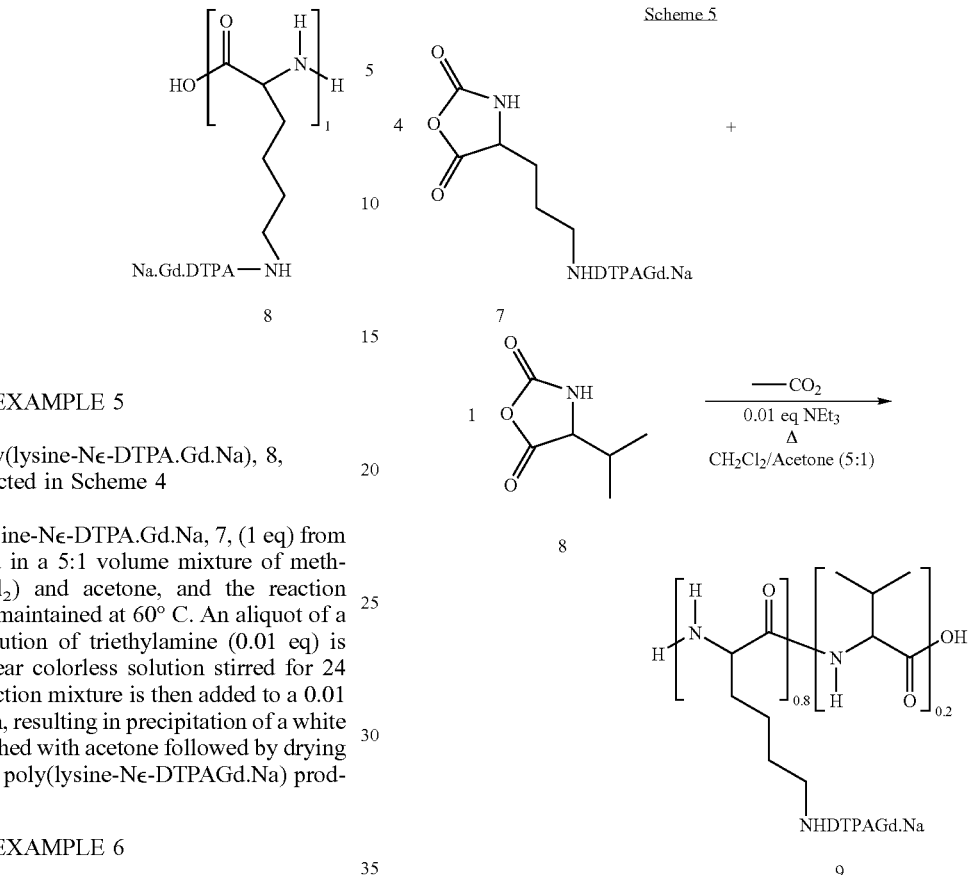

EXAMPLE 5

Synthesis of Poly(lysine-Nε-DTPA.Gd.Na), 8, Depicted in Scheme 4

A sample of NCA-lysine-Nε-DTPA.Gd.Na, 7, (1 eq) from Example 4 is dissolved in a 5:1 volume mixture of methylene chloride ($CH_2Cl_2$) and acetone, and the reaction mixture temperature is maintained at 60° C. An aliquot of a methylene chloride solution of triethylamine (0.01 eq) is then added, and the clear colorless solution stirred for 24 hours at 60° C. The reaction mixture is then added to a 0.01 M aqueous HCl solution, resulting in precipitation of a white solid, which is then washed with acetone followed by drying in vacuo to provide the poly(lysine-Nε-DTPAGd.Na) product, 8, as a white solid.

EXAMPLE 6

Alternate Synthesis of Poly(lysine-Nε-DTPA.Gd.Na, 8

A sample of NCA-lysine-Nε-DTPA.Gd.Na (2.17 g, 3.0 mmol) from Example 4 is dissolved in mixed solvent formed from 4.6 mL dioxane and 13.8 mL dimethyl sulfoxide (25% dioxane, 75% DMSO). To this solution is added 42 mL (0.03 mmol) of a dioxane solution of 10% trimethylamine, followed by stirring at 60° C. for 24 hours. After completion of the reaction, 30 mL of 0.01 N aqueous HCl acid is added to the reaction liquid. The deposited precipitate is then filtered, washed with water, and dried to provide poly(lysine-DTPA.Gd.Na), 8.

EXAMPLE 7

Synthesis of Poly(lysine-Nε-DTPAGd.Na)-(Valine) Random Copolymer 9, Depicted in Scheme 5

Samples of NCA-lysine-Nε-DTPAGd.Na, 7, (1 eq) from Example 4 and NCA-valine (0.25 eq, produced by the method described herein) are dissolved in a 5:1 volume mixture of methylene chloride ($CH_2Cl_2$) and acetone, and the reaction mixture temperature is maintained at 60° C. An aliquot of a methylene chloride solution of triethylamine (0.01 eq) is then added, and the clear colorless solution stirred for 24 hours at 60° C. The reaction mixture is then added to a 0.01 M aqueous HCl solution, resulting in precipitation of a white solid, which is then washed with acetone followed by drying in vacuo to provide the random poly(lysine-Nε-DTPAGd.Na)-(valine) copolymer 9 product, as a white solid.

EXAMPLE 8

Synthesis of Poly(lysine-Nε-DTPAGd.Na)-(valine)-(lysine-Nε-biotin), 11, Depicted in Scheme 6

(A) Synthesis of NCA-lysine-Nε-biotin, 10.

A sample of biotin (1 eq) is mixed with 1,3-dicyclohexylcarbodiimide (DCC) (1.1 eq) in dimethylformamide (DMF) (0.1M solution) and stirred for 30 mins. A sample of the 9-BBN-lysine-DTPA, 4, (1 eq) from Example 1(B) is dissolved in DMF to provide a 0.2 M solution of the amino acid derivative which is filtered and added to the activated biotin solution. Following stirring for 16 hours, a sample of ethylene diamine (EDA) (1.1 eq) is added to the reaction mixture and is heated to 60° C. for 10 mins. The volatiles are removed under reduced pressure and the residue is washed with pentanes. The residue is recrystallized from warm (~45° C.) THF/diethyl ether ($Et_2O$) to provide the lysine-Nε-biotin, 10, product as a white solid. To a methylene chloride ($CH_2Cl_2$) solution (0.1M) of lysine-Nε-biotin, 10, (1 eq) and triethylamine ($NEt_3$) (2 eq) is added triphosgene (0.3 eq) at 0° C. The reaction mixture is stirred at ambient temp for 1 hour and then the volatile organic solvents removed in vacuo. The residue is extracted with ethyl acetate (EtOAc), filtered, and the volatiles removed to afford crude, 10, which is then recrystallized from $CH_2Cl_2$/pentanes to give NCA-lysine-Nε-boitin, 10, as a white solid.

(B) Synthesis of Poly(lysine-Nε-DTPAGd.Na)-(valine)-(lysine-Nε-biotin), 11

Samples of NCA-lysine-Nε-DTPAGd.Na, 7, (4 eq) from Example 4 and NCA-valine (1 eq, produced by the method described herein) and NCA-lysine-Nε-biotin, 10, (1 eq) are dissolved in a 5:1 volume mixture of methylene chloride ($CH_2Cl_2$) and acetone, and the reaction mixture temperature is maintained at 60° C. An aliquot of a methylene chloride solution of triethylamine (0.01 eq) is then added, and the clear colorless solution stirred for 24 hours at 60° C. The reaction mixture is then added to a 0.01 M aqueous HCl solution, resulting in precipitation of a white solid, which is then washed with acetone followed by drying in vacuo to provide the random poly(lysine-Nε-DTPAGd.Na)-(valine)-(lysine-Nε-biotin) copolymer product, 11, as a white solid.

Scheme 6

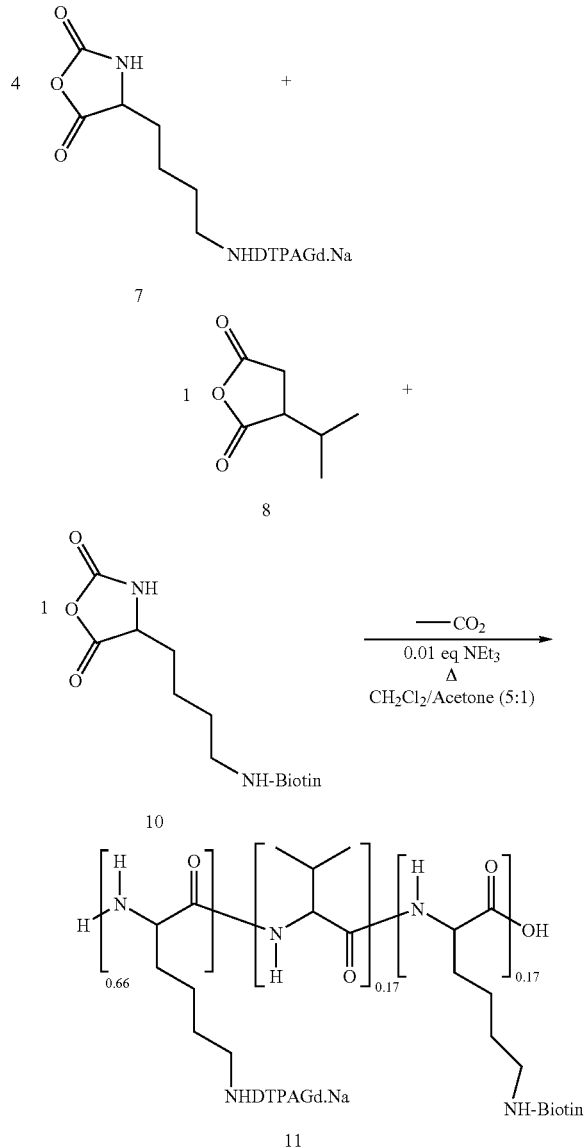

Each of the patents, patent applications, and references mentioned herein is hereby incorporated by reference in its entirety.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a polypeptide comprising monomer units (I), (II), and (III):

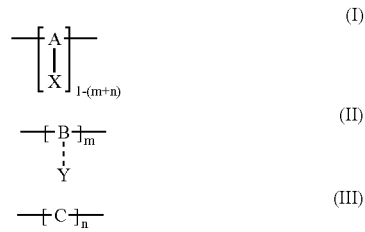

wherein said monomer units (I), (II), and (III) are randomly distributed or occurring together in said polypeptide;

wherein (A) is a first amino acid selected from the group consisting of rysine and ornithine, and (B) is a second amino acid which is the same as or different from (A); and (C) is a third amino acid different from both (A) and (B);

wherein (X) is an imaging agent conjugated to said first amino acid (A), wherein said imaging agent (X) is selected from the group consisting of organic nitroxyl radicals, iodinated organic species, chelator moieties, and protected chelator moieties;

wherein said imaging agent (X) is optionally complexed with a paramagnetic cation or a radioactive cation when said selected imaging agent is a chelator moiety;

wherein said imaging agent (X) is optionally conjugated to said first amino acid (A) through a linking group selected from the group consisting of $C_1$ to $C_{20}$ aryl, heteroaryl, linear, branched or cyclic alkyl groups, wherein one or more $CH_2$ may be fully or partly substituted with —S—, —O—, —N—, —CH=CH—, aryl, heteroaryl, linear, branched or cyclic alkyl or —C≡C—, or combination thereof;

wherein m is the mole fraction of said monomer units (II) having a numeral value ranging from 0 to about 0.99; and n is the mole fraction of said monomer units (III) having a numeral value ranging from 0 to about 0.99, wherein n>0 only when m>0, wherein the sum of m+n≦0.99;

and wherein 1−(m+n) is the more fraction of said monomer units (I);

said method comprising the steps of
(a) providing said first amino acid (A) conjugated to said imaging agent (X); and when m>0 providing said second amino acid (B);
and when n>0 providing said third amino acid (C);
(b) contacting said first amino acid (A) conjugated to said imaging agent (X) with phosgene or triphosgene to form the N-carboxyanhydride of said first amino acid (A) conjugated to said imaging agent (X), and when m>0, contacting said second amino acid (B) with phosgene or triphosgene to form the N-carboxyanhydride of said second amino acid (B); and when n>0, contacting said third amino acid (C) with phosgene or triphosgene to form the N-carboxyanhydride of said third amino acid (C); and
(c) forming said polypeptide
  (i) when m+n=0, by polymerizing said N-carboxyanhydrlde of said first amino acid (A) conjugated to said imaging agent (X) to form said polypeptide, wherein said polypeptide is a homopolymer having monomer units (I); but
  (ii) when m>0 and n=0,
  (iia) by polymerizing said N-carboxyanhydride of said first amino acid (A); conjugated to said imaging agent (X) to form monomer units (I) occurring together, and polymerizing said N-carboxyanhydride of said second amino acid (B) to form monomer units (II) occurring together, followed by the polymerization of monomer units (I) with monomer units (II) to form said polypeptide, wherein said polypeptide is a block polymer; or
  (iib) by simultaneously polymerizing said N-carboxyanhydride of said first amino acid (A) conjugated to said imaging agent (X) with said N-carboxyanhydride of said second amino acid (B) to form said polypeptide, wherein said monomer units (I) and (II) are randomly distributed, and wherein said polypeptide is a random copolymer; but
  (iii) when m>0 and n>0,
  (iiia) by polymerizing1 said N-carboxyanhydride of said first amino acid (A) conjugated to said imaging agent (X) to form monomer units (I) occurring together, and polymerizing said N-carboxyanhydride of said second amino acid (B) to form monomer units (II) occurring together, and polymerizing said N-carboxyanhydride of said third amino acid (C) to form monomer units (III) occurring together; or
  (iiib) by simultaneously polymerizing said N-carboxyanhydride of said first amino acid (A) conjugated to said imaging agent (X) with said N-carboxyanhydride of said second amino acid B and with said N-carboxyanhydride of said third amino acid (C) to form said polypeptide, wherein said monomer units (I), (II), and (III) are randomly distributed, and wherein said polypeptide is a random copolymer; or
  (iiic) by polymerizing one of said N-carboxyanhydride of said first amino acid (A) conjugated to said imaging agent (X) or said N-carboxyanhydride of said second amino acid (B) or said N-carboxyanhydride of said third amino acid (C) to form monomer units (I), (II), or (III) occurring together, followed by the simultaneous polymerization of said monomer units (I), (II), or (III) occurring together with whichever two of said N-carboxyanhydride of said first amino acid (A) conjugated to said imaging agent (X) or said N-carboxyanhydride of said second amino acid (B) or said N-carboxyanhydride of said third amino acid (C) remain after formation of said monomer units (I), (II), or (III) occurring together, to form said polypeptide, wherein said polypeptide is a mixed copolymer comprising monomer units (II) and (III) randomly distributed between said monomer units (I) occurring together or is a mixed copolymer comprising monomer units (I) and (III) randomly distributed between said monomer units (II) occurring together, or is a mixed copolymer comprising monomer units (I) and (II) randomly distributed between said monomer units (III) occurring together.

2. The method of claim 1, wherein said imaging agent (X) is a chelator moiety selected from the group consisting of diethylenetriamine pentaacetic acid (DTPA), triethylenetetraminehexaacetic acid (TTHA), ethylenedlamlnetetraacetio acid (EDTA), 1,2-diaminocyclohexane-N,N,N',N'-tetraacetic acid, N,N'-di-(2-hydroxybenzyl)ethylenediamine (HBED), N-(2-hydroxyethyl)ethylenediaminetriacetic acid, nitrilotriacetic acid, ethylene-bis(oxyethylenenitrilo)tetraacetic acid (EGTA), 1,4,7,10-tetraazacyclododecane-N,N',N'',N'''-tetraacetic acid (DOTA), 1,4,7,10-tetraazacyclododecane-N,N',N''-triacetic acid (DO3A), 1,4,7-tris(carboxymethyl)-10-(2'-hydroxy)propyl)-1,4,7,10-tetraazocyclodecane (HP-DO3A), 1,4,7-triazacyclonane-N,N',N-triacetic acid (NOTA), 1,4,8,11-tetraazacyclotetradecane-N N', N'', N'''-tetraacetic acid (TETA).

3. The method of claim 2, wherein said selected chelator moiety (X) is complexed with a paramagnetic cation selected from the group consisting of gadolinium (III), dysprosium (III), holmium (III), europium (III), iron (III), and manganese (II).

4. The method of claim 2, wherein said selected chelator moiety (X) is complexed with a radioactive cation selected from the group consisting of copper (II), indium (II), indium (III), and yttrium (III).

5. The method of claim 1, wherein said imaging agent (X) is a chelator moiety selected from the group consisting of moieties having formulae (IV), (V), (VI), and (VII):

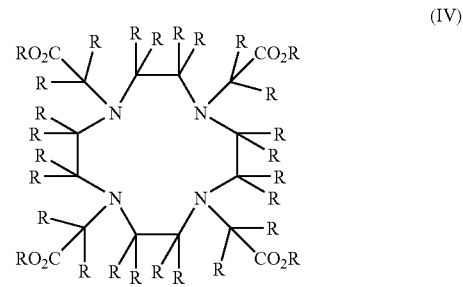

(IV)

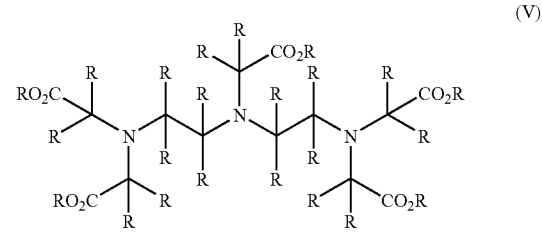

(V)

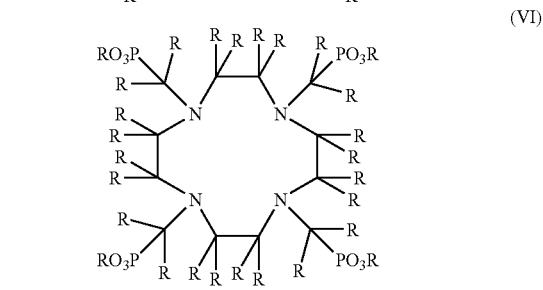

(VI)

-continued

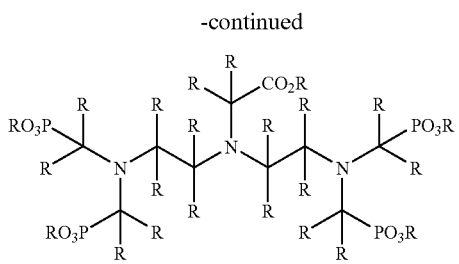

(VII)

wherein each R is selected from the group consisting of $C_1$ to $C_{20}$ aryl; heteroaryl; linear, branched and cyclic alkyl; linear, branched and cyclic alkyl; substituted with —S—, —O—, —N—, —CH=CH—, aryl, heteroaryl, linear, branched or cyclic alkyl, —C≡C—; and combinations thereof.

6. The method of claim 5, wherein said selected chelator moiety (X) is complexed with a paramagnetic cation selected from the group consisting of gadolinium (III), dysprosium (III), holmium (III), europium (III), iron (III), and manganese (II).

7. The method of claim 5, wherein said selected chelator moiety (X) is complexed with a radioactive cation selected from the group consisting of copper (II), indium (II), indium (III), and yttrium (III).

8. The method of claim 1, wherein said imaging agent (X) is an organic nitroxyl radical selected from the group consisting of 2,2,6,6-tetramethyl-1-piperidinyloxy (TEMPO), 4-hydroxy-2,2,6,6-tetramethyl-1-piperidinyloxy (4-OH-TEMPO), and 4-amino-2,2,6,6-tetramethyl-1-piperidinyloxy (4-$NH_2$-TEMPO).

9. The method of claim 1, wherein said imaging agent (X) is an iodinated organic species selected from the group consisting of iohexol and iodixanol.

10. The method of claim 1, wherein said first amino acid (A) is lysine, and said selected imaging agent (X) is diethylenetriamine-pentaacetic acid (DTPA).

11. The method of claim 10, wherein said DTPA is complexed with gadolinium (III).

12. The method of claim 11, wherein m=0 and n=0.

13. The method of claim 11, wherein m>0 and n=0, and said second amino acid (B) is lysine.

14. The method of claim 1, wherein m>0 and n=0, and said second amino acid (B) is selected from the group consisting of lysine, ornithine, alanine, arginine, asparagine, aspartic acid, cysteine, glutamine, glutamic acid, glycine, histidine, isoleucine, leucine, methionine, phenylalanine, proline, serine, threonine, tryptophan, tyrosine, and valine.

15. The method of claim 1, wherein m>0 and n>0, and said second amino acid B and third amino acid C are each independently selected from the group consisting of lysine, ornithine, alanine, arginine, asparagine, aspartic acid, cysteine, glutamine, glutamic acid, glycine, histidine, isoleucine, leucine, methionine, phenylalanine, proline, serine, threonine, tryptophan, tyrosine, and valine.

16. The method of claim 1, wherein m>0 and n≧0, and wherein said second amino acid (B) is covalently bonded to said pendant side chain (pre)targeting moiety (Y), wherein said pendant (pre)targeting moiety (Y) is selected from the group consisting of folic acid, cobalamine, galactose, glucose, mannose, mannitol, peptides, estrogens, folate, biotin, PNAs, aptamers, and organic molecules used in disease therapy.

17. The method of claim 1, wherein each polymerization in step (c) occurs in the presence of a polymerization initiator selected from group consisting of low valent transition metal initiators.

18. The method of claim 17, wherein said low valent transition metal initiator is selected from the group consisting of bipyNi(COD), $(PMe_3)_4Co$, and $(PMe_3)_4Fe$, wherein bipy is 2,2'-bipyridyl; COD is 1,5-cyclooctadiene; and Me is methyl.

19. The method of claim 1, wherein each polymerization in step (c) occurs in the presence of a polymerization initiator selected from the group of alkali metal hydroxides, alkali metal alkoxide initiators, alkali metal initiators of diols, and amines.

20. The method of claim 1, wherein said first amino acid (A) conjugated to said imaging agent (X) provided in step (a) is prepared by the steps of
  (i) condensing said imaging agent X with a borate-protected first amino acid (A) to form a borate-protected first amino acid A conjugated with said imaging agent (X);
  (ii) deprotecting said borate-protected first amino acid (A) conjugated with said imaging agent (X) in the presence of a diamine or HCl to form said first amino acid A conjugated to said imaging agent (X).

21. A method of preparing a polypeptide comprising monomer units (I) and (II):

wherein said monomer units (I) and (II) are randomly distributed or occurring together in said polypeptide;
wherein (A) and (B) are both lysine; (X) is DTPA; (X.Gd) is DTPA complexed with gadolinium (III); m is the mole fraction of monomer units (II) having a value ranging from 0 to about 0.99; and 1-m is the mole fraction Of monomer units (I);
said method comprising the steps of:
  (a) providing said lysine (A) conjugated to said DTPA (X) complexed with said gadolinium (III) (Gd), and when m>0 providing said lysine (B);
  (b) contacting said lysine (A) conjugated to said DTPA (X) complexed with gadolinium (III) (Gd) with phosgene or triphosgene to form the N-carboxyanhydride of said lysine (A) conjugated to said DTPA (X) complexed with gadolinium (III) (Gd), and when m>0, contacting said lysine (B) with phosgene or triphosgene to form the N-carboxyanhydride of said lysine (B); and
  (c) when m=0, polymerizing said N-carboxyanhydride of said lysine (A) conjugated to said DTPA (X) complexed with gadolinium (III) (Gd) to form said polypeptide, wherein said polypeptide is a homopolymer having monomer units (I),
  but when m>0 polymerizing said N-carboxyanhydride of said lysine (A) conjugated to said DTPA (X) complexed with gadolinium (III) (Gd) to form monomer units (I) occurring together, and polymerizing said N-carboxyanhydride of said lysine (B) to form monomer units (II) occurring together, followed by the polymerization of monomer units (I) with monomer units (II) to form said polypeptide, wherein said monomer units (I) and (II) each occur together, and wherein said polypeptide is a block polymer, or when m>0, simultaneously polymerizing said N-carboxyanhydride of said lysine (A) conjugated to said DTPA (X) complexed with gadolinium (III) (Gd) with said N-carboxyanhydride of said lysine (B) to form said polypeptide, wherein said monomer units (I) and (II) are randomly distributed, and wherein said polypeptide is a random copolymer.

22. The method of claim 21, wherein m=0.

23. The method of claim 21, wherein the value of m ranges from about 0.01 to about 0.99.

24. The method of claim 23, wherein the value of m ranges from about 0.1 to about 0.4.

25. The method of claim 24, wherein the value of m ranges from about 0.2 to about 0.3.

26. The method of claim 21, wherein each polymerization in step (c) occurs in the presence of a polymerization initiator selected from group consisting of low valent transition metal initiators.

27. The method of claim 26, wherein said low valent transition metal initiator is selected from the group consisting of bipyNi(COD), $(PMe_3)_4Co$, and $(PMe_3)_4Fe$, wherein bipy is 2,2'-bipyridyl; COD is 1,5-cyclooctadiene; and Me is methyl.

28. The method of claim 21, wherein each polymerization in step (c) occurs in the presence of a polymerization initiator selected from the group of alkali metal hydroxides, alkali metal alkoxide initiators, alkali metal initiators of diols, and amines.

* * * * *